United States Patent [19]

Leonard

[11] 4,122,837
[45] Oct. 31, 1978

[54] BODY SURFACE CONTOUR DEFORMATION

[76] Inventor: Loren W. Leonard, 162 Plantation, Houston, Tex. 77024

[21] Appl. No.: 710,711

[22] Filed: Aug. 2, 1976

[51] Int. Cl.$^2$ .............................................. A61B 5/10
[52] U.S. Cl. ...................................................... 128/2 S
[58] Field of Search ............. 128/2 S, 2.05 D, 2.05 E, 128/2.05 P, 2.05 N, 2.05 G, 2.05 S; 73/379, 406, 409, 410, 388 R

[56] References Cited

U.S. PATENT DOCUMENTS

| | | | |
|---|---|---|---|
| 1,561,116 | 11/1925 | Silliman | 128/325 |
| 2,199,408 | 5/1940 | La Liberte | 128/2.05 G |
| 2,831,478 | 4/1958 | Uddenberg et al. | 128/2 S |
| 3,704,708 | 12/1972 | Iberall | 128/2.05 E |
| 3,853,118 | 12/1974 | Schendel | 128/2 S |
| 3,867,925 | 2/1975 | Ersek | 128/2.05 S |

Primary Examiner—Robert W. Michell
Assistant Examiner—Michael H. Thaler
Attorney, Agent, or Firm—Bard & Groves

[57] ABSTRACT

A deformation detector for use with IV needles or catheters inserted into the human body is disclosed. Swelling and deformation attributal to other sources is also detectable. The apparatus in particular has a preferred embodiment which comprises a generally rectangular body enclosing an air chamber. The chamber is rectangular and or one face thereof, a thin diaphragm is attached. The diaphragm is joined by a suitable adhesive to the body adjacent to a IV needle or catheter. In the event of swelling as a result of improper operation of the injection which swelling, while hardly visible to the eye, is detected by conformance of the thin diaphragm adhered to the skin. Swelling or edema from other sources is similarly detectable. Swelling changes the internal air volume of the chamber and thereby forms a pneumatic signal supplied through a tubing to a transducer or recording device. This is used to form a signal.

4 Claims, 4 Drawing Figures

BODY SURFACE CONTOUR DEFORMATION

BACKGROUND OF THE INVENTION

Attempts have been made in the past to detect improper operation of a needle or catheter as evidenced by U.S. Pat. No. 3,853,118. Devices of this sort are limited in their capability and, in particular, point out some of the medical problems associated with intravenous infusions into the human body.

Customarily, IV infusions are achieved by inserting a needle or catheter of the proper gage cannula typically just under the skin and into a suscutaneous vein. Two or three problems typically occur. At the time of insertion of the cannula, the medical personnel may believe that it was inserted without lateral movement into a presumably straight vein when in fact the point was laterally misaligned or otherwise contacted against the vein wall thereby forming tears or scratches on interior vein walls which are undesirable. The cannula may be too large for the vein. Further, venipuncture site may not seal around the cannula. On insertion through the layers of subsurface skin (dermis and epidermis) including the wall of a vein leakage (extravasation) may occur back along the cannula. Even if the cannula is prefectly placed in the vein with no problems, subsequent patient movement can inadvertently force the cannula through a vein to infuse the IV fluid into body tissue (otherwise known as infiltration). This leakage between layers of the skin sometimes is very harmful because the IV solution is delivered to the wrong part of the body of the patient typically causing phlebitis or thrombophlebitis. A further problem is enlargement of the small openings formed by the cannula and resultant chemical or hydraulic action of the IV solution. That is to say, the cannula is correctly inserted but after it has been in place for a period of time, extravasation along the pinhole sized openings formed in the path of the cannula may occur and thereby cause swelling to be formed in the near vicinity.

Most of the problems which arise with difficulty in IV infusions are evidenced with a slight early swelling in the immediate area. The swelling is very slight and difficult to observe in the beginning. However, it is at this juncture that remedial steps are most effective. Given the situation where a person has been hospitalized for a substantial period of time and has been given many IV injections, the nursing personnel typically have great difficulty in maintaining and keeping open veins for repetitive infusions. If a problem arises with the IV infusion at the site of needle insertion, it takes several days, even weeks in an older person, for the localized bruising and trama to heal. This forces the nursing personnel to seek another site for IV infusions, and upon an extended hospitalization, such sites are not readily available.

Other sources of edema exist. Causes are numerous and are varied as medical problems but typical causes include phlegmasia, pulmanary edema, venostasis, vascular occlusions, trauma, surgical incisions, contusions, sprains, fractures, and so on. These are noted by competent nursing personnel who detect color changes or localized swelling, normally achieved by a combination of visual inspection and localized palpation.

In summary, the exemplary problems point out why proper IV infusions are desirable; proper IV infusions assure that the patient receives the desired infusion in timely fashion, side effects are eliminated, and the personnel does not lose infusion sites, an especially critical problem in long term hospitalizations.

With the foregoing edema problems in view, the present apparatus is a device which detects swelling in the near vicinity of the site of an IV infusion or some other source of edema. It is sensitive and therefore able to provide a prompt and early indication of swelling so that remedial steps can be taken quickly to avoid aggrevated problems. The signal is provided sufficiently promptly to enable removal of the needle or aleviation of the source of edema so that the problem is not aggrevated by continued swelling and accumulation of IV fluids at an unintended location. If the infusible is not delivered to the intended location, the medication may be lost and the planned program of treatment will be delayed and recovery will be delayed. More importantly, this apparatus is able to be attached at any point of the body where a needle is inserted into the human body. It can be attached close to an incision or fracture beneath a bandage or cast. Typically, needles are inserted in the veins of the arms or legs but the apparatus is not limited to those locations. It is able to be attached without the use of a tourniquet or pressure cuff extending around the limb or trunk of the body. Moreover, it can be left unattended and yet forms a signal which sounds through an appropriate alarm device an alarm to nursing personnel. As a result of the use of the present device, localized trauma and edema in the vicinity of the site of an IV infusion or other edema is thereby avoided and the problems associated with a localized injury are thereby either reduced or avoided.

SUMMARY OF THE DISCLOSURE

This disclosure is directed to an adhesive rectangular chamber which is attached to the skin of a person at the site of an IV infusion or elsewhere near suspected edema. It is constructed with an outer rigid body member defining a chamber which is open on one face and a thin adhesive layer is affixed across the face. This adhesive layer attaches to the body and takes the form or shape of the body. The adhesive layer closes over the chamber. The chamber formed in the outer body captures a certain volume of air. As swelling occurs, the thin adhesive membrane deflects into the chamber thereby changing air pressure in the chamber. The chamber is communicated by a small passage into a tubing which is connected to a pressure transducer which forms a signal indicative of a change in pressure. Other geometric shapes of chamber may be used.

DESCRIPTION OF THE PREFERRED EMBODIMENT

Figure 1:
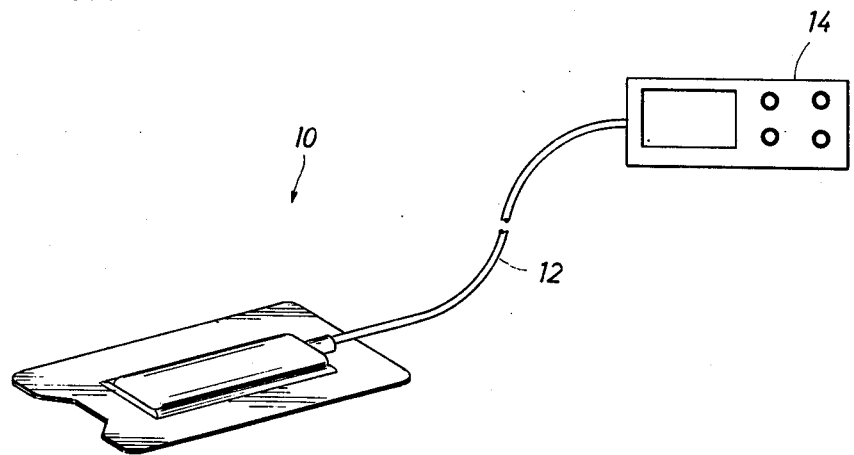
FIG. 1 is a perspective view of the IV swelling detector of the present disclosure showing a flexible pneumatic tube extending to a signal transducer.
Figure 4:
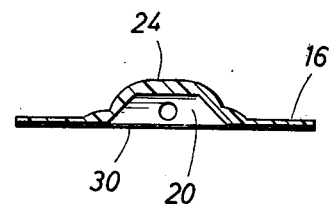
FIG. 4 is a transverse sectional view through the apparatus showing additional details of construction of the chamber.
Figure 3:
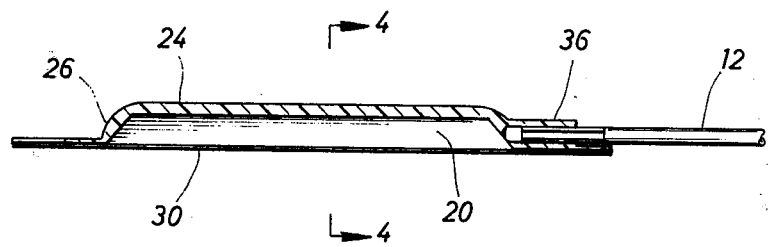
FIG. 3 is a lengthwise sectional view along the center line of the IV swelling detector of the present apparatus showing the thin membrane which attaches to one side of the chamber for communicating swelling of a patient which is converted into a pressure signal in a conduit extending from the chamber.

Attention is first directed to FIG. 1 of the drawings where the IV swelling detector of the present invention is identified generally by the numeral 10. The edema detector will be described for detection of swelling in the specified example and other examples of its use will be set forth later. It is connected by way of a small flexible hollow tube 12 to an alarm device 14. The apparatus operates, and will be described, by forming small pressure signals in the tubing 12 which are communicated to the alarm device 14. The alarm device itself is responsive to a small change in pressure, and if the change is of specified size, it forms an alarm signal such as the sounding of a bell. This summons nursing personnel to inspect for swelling and to enable them to remove, if necessary, the needle or catheter for insertion at another location. This particularly quickly enables the nursing personnel to either locate a new site for the needle or to otherwise determine that there is no significant problem utilizing their experience and training. In any case, the present apparatus serves a valuable function in that it forms a signal indicative of localized swelling at the location of a needle or catheter.

Figure 2:
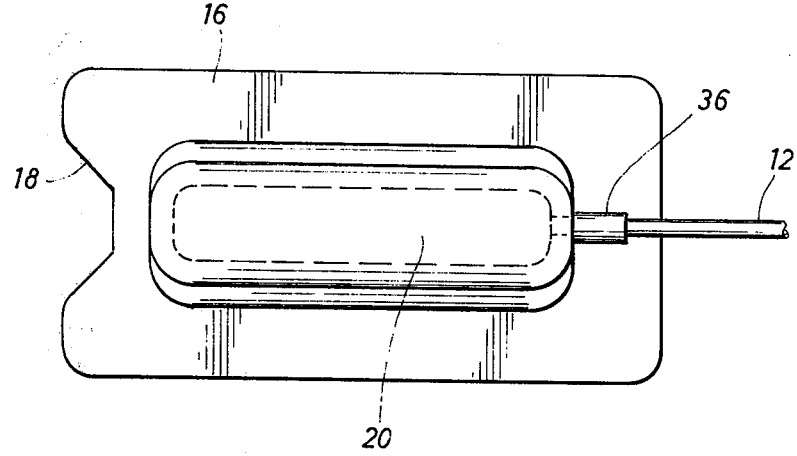
FIG. 2 is a section plan view of the IV swelling detector of the present invention showing details of construction of an internal chamber which is closed over by a thin membrane.

Going to FIG. 2 of the drawings, the numeral 16 identifies a surrounding flat skirt which is generally rectangular except that a notch 18 is removed from one end. The surrounding skirt defines a generally flat surface as illustrated in the drawings. A needle or catheter which typically will measure from about 3 to 10 centimeters in length extending from a fitting is inserted at the appropriate location into a patient. The rectangular skirt is positioned immediately adjacent to the needle with the actual point of insertion located at the notch 18. The skirt serves as an anchor or relatively fixed platform for the device. The notch can be omitted for other edema detection purposes.

The needle is approximately parallel and located along a center line of the apparatus, and hence it is positioned just beneath an internal chamber 20 centered in the surrounding skirt. The chamber 20 is approximately rectangular and is centered in the surrounding skirt 16. The notch 18 enables the chamber 20 to be positioned in an overlying relationship above the catheter adjacent to the point of insertion. In other words, the full length of the needle which is inserted into the body of the patient is located just beneath the chamber 20. Swelling normally occurs in the near vicinity of the chamber 20 and accordingly, the surrounding skirt is notched to enable the chamber to be located as close as possible to the full length of the needle. The apparatus connected to the catheter or cannula normally lays against the body, often aided by the use of adhesive tape to fix it in location. This limits movement of the needle or catheter and the possibility of traumatic injury as a result of the unwanted movement. Moreover, the apparatus is able to be used at any point where a needle or catheter is inserted. This is particularly helpful in that it is not limited to attachment to the limbs of a person through the use of a surrounding pressure cuff or other strap mechanism.

The apparatus 10 is preferably formed of two major components, one of which is an outer body portion 24. The portion 24 incorporates the surrounding skirt and, at the central portions thereof, a raised shoulder defines an upstanding wall portion 26 which captures a certain air volume therewithin to define the chamber 20. The outer body portion 20 is preferably formed of a fairly rigid plastic material about 10 times or more stiffer than the diaphragm described below. The chamber itself is in the form of a generally rectangular volume. The sidewall 26 which defines the surrounding edge of the chamber is preferably formed at an angle to enable ease of removal from an injection molding machine. This enables easy removal by the incorporation of a suitable draft angle at the sidewall 26. The chamber itself measures up to about 10 centimeters in length, and typically is in the range of about 2 or 3 centimeters in width. While it can be larger, it is not necessary that a larger chamber be formed. The chamber is hollow and up to about 1 centimeter in depth. The chamber itself is thus defined on five sides by the outer body portion 24 and is closed over by a thin diaphragm 30 made of flexible plastic material of about 3 mil thickness.

The diaphragm 30 is adhesively joined to the surrounding skirt 16. It is stretched tight over the chamber, and upon closing against the outer body 24, thus defines the chamber. The diaphragm 30 is formed of relatively thin material, and typically is up to about 10 mils in thickness and has a tensile strength sufficient to flex with the skin of the patient, and elasticity to deflect with swelling. Thinner material can be used although materials in the range of 1 or 2 mils are perhaps a bit on the fragile side. A suitable thin adhesive is placed on the outer surface of the diaphragm 30. The adhesive fixes the diaphragm to the patients body.

The adhesive selected is preferably a type which is non-toxic, non-allergenic, and non-pyrogenic. Preferably, the adhesive is placed on the diaphragm 30 at the time of manufacture. The tacky surface is then covered with a disposable wrapper which protects the adhesive during manufacture, shipment and storage. The wrapper is easily removed at the time of installation. This exposes the tacky surface which then enables the swelling detector 10 to be quickly and temporarily attached to the body of a patient. To this end, the outer wrapper is peeled from the diaphragm 30 and the apparatus is then ready for installation. An alternate means of attachment is one or two strips of conventional tape. Alternately, the entire body of the apparatus can be wedged beneath a bandage or cast against the patient.

The outer body 24 is formed with a hollow fitting 36 at one end. The fitting 36 extends through the sidewall 26. An axial passage from the chamber 20 to the exterior is thus defined. The fitting 36 is sized to receive the pneumatic tube 12 which is inserted into it. The tube 12 is preferably joined to the fitting 36 in a leak proof connection. This enables the tube 12 to transfer elsewhere a pneumatic signal formed by the change of volume in the chamber 20. Pressure changes of 0.04 psi and smaller caused by edema have been detected.

It is best to consider the operation of the device to enhance the explanation. The device is packaged as described above with a disposable wrapper which is peeled from the diaphragm 30. At the time of installation, the needle is first inserted in the patient. The needle serves as a marker limiting the location of the swelling detector 10. The needle thus defines the center line position, and the diaphragm face is placed over the point of insertion and the immediate vicinity. The wrapper is peeled from the diaphragm 30, and the swelling detector 10 is gently but firmly adhesively joined to the body of the patient. At this juncture, substantially the entire length of the needle is located so that any edema associated with the use of the needle is detectable by deformation or deflection of the diaphragm. The tubing 12 is connected to the alarm device 14. The chamber is relatively stiff but yet is bendable. This enables the entire device to be bent or wrapped around the arm of a small person (e.g., a baby) and of course the diaphragm is deformed accordingly. This does not detract from use of the device; rather, it enables the monitor to be affixed to the patient even though the arm or leg is extremely small. Sensitivity is increased by bending the detector.

After attachment, the IV infusion proceeds with the passage of time. In the event that swelling occurs for any reason, the swelling is manifested at the site of the needle by localized swelling. The swelling is very slight at first as might occur by the accumulation of only a small portion of the injectable suscutaneously in the patient. The device is sensitive to edema having a volumetric displacement of a very small drop, or about 65 microliters change. Should a less sensitive device be desired, the alarm device can be calibrated to sound on larger pneumatic changes. This slight and localized swelling is nevertheless sufficient to deform the diaphragm 30. When the diaphragm is deformed, it is forced into the chamber 20 to compress air. This reduces the volume of the chamber 20. As the volume is reduced, an air pressure change is forced from it through the tubing 12. The pressure change forced into the tubing 12 thus becomes a pneumatic signal communicated through the tubing to an alarm device 14. An alarm is sounded. This quickly brings nursing personnel to attend the patient and particularly to inspect the area surrounding the site of the IV needle. Speed of detection is many fold over the other techniques.

The inspection is easily done by quickly removing the swelling detector. The nursing personnel can then visually inspect the immediate area for discoloration, localized swelling, bruising, or the like. The apparatus is advantageous in that it furnishes an early warning of swelling and trauma. The early warning is particularly useful in that it enables early removal of the needle. If the situation is detected before the swelling has become extreme, the localized injury can be arrested to avoid the long curative period required to heal the localized injury. For instance, early detection of an improper IV infusion can prevent the type of bruising and vein damage which typically can occur and which often will require weeks to heal in older patients. This is an invaluable aid for those who are hospitalized for great lengths of time in that it keeps their readily accessible veins available for repeated use as infusion sites.

Separate and apart from the foregoing, the edema detector can be used to detect swelling from other sources. As an example consider a cast applied to the upper leg. The swelling detector can be slipped under the cast and left there. It is sensitive to the swelling associated with fractures and sprains and will detect the swelling to sound an alarm. The cast can thereafter be loosened to relieve the swelling. The detector can be attached to the top of the instep of the foot and ankle to detect swelling due to venous stases. The skirt around the chamber is sized to extend beyond the area of expected swelling and thus serves as a type of reference. This will enable the device to extend beyond the localized swelling. This avoids swelling which lifts the entire detector.

The apparatus of the present invention has been described and in particular the preferred embodiment has been set forth. The preferred embodiment is subject to construction in a different fashion, all in accordance with the scope of the claims which are appended hereto.

I claim:

1. A detector for detecting body swelling or edema, comprising:
    a generally rectangular chamber defined by a stiff portion having on one side thereof a pliant membrane which membrane has a deflectable surface of specified width and length which is exposed for surface contact against a selected area of a patient and which membrane conforms to and deflects with localized swelling or edema of the patient;
    the stiff portion of the chamber incorporating a protruding lip extending outwardly along four edges in a common plane;
    a side wall appended to said lip and extending above the membrane and which side wall is interrupted by an opening means connected through a hollow tube adapted to be connected to an alarm device;
    and wherein said surrounding lip is notched at a portion thereof to define an alignment means for a needle or catheter.

2. The apparatus of claim 1 including a membrane of between 1 and 10 mils thick.

3. The apparatus of claim 2 wherein said chamber and said membrane are formed of a material enabling said chamber to be bent to conform to a body shape exemplified by an arm, and yet wherein said chamber is, relative to said membrane, relatively stiff to support and position said membrane.

4. The apparatus of claim 3 including a skin contact adhesive on one surface of the membrane.

* * * * *